United States Patent
Palumbo et al.

(10) Patent No.: US 6,749,923 B1
(45) Date of Patent: *Jun. 15, 2004

(54) MOISTURE VAPOR PERMEABLE COMPOSITE STRUCTURE AND THE UTILIZATION THEREOF IN ABSORBENT ARTICLES

(75) Inventors: Gianfranco Palumbo, Bad Homburg (DE); Italo Corzani, Chieti (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/701,998

(22) PCT Filed: Jun. 1, 1999

(86) PCT No.: PCT/IB99/00978

§ 371 (c)(1),
(2), (4) Date: Dec. 6, 2000

(87) PCT Pub. No.: WO99/64237

PCT Pub. Date: Dec. 16, 1999

(30) Foreign Application Priority Data

Jun. 9, 1998  (EP) ............................................. 98110593

(51) Int. Cl.[7] .............................. B32B 3/10; A61F 13/15
(52) U.S. Cl. ......................... 428/131; 442/62; 604/367
(58) Field of Search .......................... 428/131; 442/62; 604/367

(56) References Cited

U.S. PATENT DOCUMENTS

| | | | | |
|---|---|---|---|---|
| 4,758,239 A | | 7/1988 | Yeo et al. .................... 604/366 |
| 4,857,393 A | * | 8/1989 | Kato et al. ................... 428/289 |
| 5,683,815 A | * | 11/1997 | Leiss ........................ 428/424.4 |
| 5,827,252 A | * | 10/1998 | Werenicz et al. ............ 604/367 |
| 6,071,450 A | * | 6/2000 | Topolkaraev et al. .. 264/173.12 |
| 6,495,612 B1 | * | 12/2002 | Corzani et al. ............. 523/105 |
| 6,498,201 B1 | * | 12/2002 | Corzani et al. ............. 523/111 |
| 6,534,561 B1 | * | 3/2003 | Palumbo et al. ............ 523/111 |

FOREIGN PATENT DOCUMENTS

| | | |
|---|---|---|
| EP | 0 295 694 A2 | 12/1988 |
| EP | 0 539 604 A1 | 5/1993 |
| GB | 1 341 605 | 12/1973 |
| WO | WO 96/25902 | 8/1996 |

* cited by examiner

*Primary Examiner*—Harold Pyon
*Assistant Examiner*—Patricia L. Nordmeyer
(74) *Attorney, Agent, or Firm*—Frank Taffy; Kevin C. Johnson; Leonard W. Lewis

(57) ABSTRACT

The present invention relates to liquid impermeable moisture vapor permeable composite structure comprising a specific thermoplastic film which is thinly coated onto a support layer. The composite structures of the present invention can find a variety of applications, wherein moisture vapor permeability is desirable for example within absorbent articles such as diapers, sanitary napkins, panty liners and incontinence products, protective bedding covers, protective clothing and the like.

7 Claims, No Drawings

MOISTURE VAPOR PERMEABLE COMPOSITE STRUCTURE AND THE UTILIZATION THEREOF IN ABSORBENT ARTICLES

FIELD OF THE INVENTION

The present invention relates to liquid impermeable moisture vapour permeable composite structures comprising a specific thermoplastic film which is thinly coated onto a support layer. The composite structures of the present invention can find a variety of applications, wherein moisture vapour permeability is desirable for example within absorbent articles such as diapers, sanitary napkins, panty liners and incontinence products, protective bedding covers, protective clothing and the like.

BACKGROUND OF THE INVENTION

Thermoplastic films which provide a liquid barrier in addition to providing moisture vapour permeability are known in the art. Particularly preferred are hydrophilic continuous films that do not allow the flow of moisture vapour through open pores or apertures in the material, but do transfer substantial amounts of moisture vapour through the film by absorbing water on one side of the film where the moisture vapour concentration is higher, and desorbing or evaporating it on the opposite side of the film where the moisture vapour concentration is lower. Compositions used to form hydrophilic continuous, moisture vapour permeable, liquid impervious films are also said to be moisture vapour permeable, liquid impervious.

For example WO 95/16746 discloses films prepared from mixtures of a) block copolyether ester, block copolyether amides (e.g. Pebax™) and or polyurethane and b) thermoplastic polymer which is incompatible with a, and c) a compatibiliser. The films are liquid impermeable and have moisture vapour permeability of about 700 g/m$^2$/day. Also, U.S. Pat. No. 5,447,783 discloses a vapour permeable water resistant multi component film structure having at least three layers. The outer layers are hydrophobic copolyetherester elastomers having a thickness of 1.3–7.6 micrometers and a WVTR of 400–2500 g/m$^2$/24 hrs. and the inner layer is a hydrophilic copolyetherester elastomer having a thickness of 7.6–152 micrometers and a WVTR of at least 3500 g/m$^2$/24 hrs.

U.S. Pat. No. 5,445,875 discloses a waterproof, bloodproof and virusproof breathable laminate. The laminate comprises a woven/nonwoven fabric and an extruded film such as Hytrel™ having a thickness of about 1 mil.

However, whilst these films are desirable in so far as their moisture vapour transport rate is concerned, these films tend to lack other desirable physical characteristics such as tear strength and flexibility depending on the end usage envisioned.

Attempts to address this problem have resided in providing the polymers on a supportive substrate which provides the required physical attributes. Such composites are described for example in U.S. Pat. No. 5,599,610 which discloses tri-laminated fabric for surgical gowns comprising outer layers of woven fabric and an inner layer of a microporous polyurethane membrane. The microporous film has a thickness of 12–55 micrometers and a MVTR of 1100 g/m$^2$/24 hrs. upright and 5500 g/m$^2$/24 hrs. inverted (ASTM E96-B). Polyether-polyurethane adhesive is used to join the layers.

Similarly, U.S. Pat. No. 5,532,053 discloses a high moisture transmission medical film which can be laminated onto a nonwoven material. The laminate film comprises a first layer of polyetherester copolymer and second and third layers selected from a specified group of polymers. The film has a MVTR of greater than 750 g/m$^2$/24 hrs. (ASTM F1249) and a thickness of less than 1 mil (25.4 micrometer) preferably 0.6 mm to 0.75 mm (15–19 micrometers).

U.S. Pat. No. 4,938,752 discloses absorbent articles comprising films of copolyether esters which have reduced water permeability, a water vapour permeability of 500 g/m$^2$/24 hrs. (as measured in a specified described test) and a thickness of 5–35 micrometers. There is no disclosure of a supportive substrate.

U.S. Pat. No. 4,493,870 discloses a flexible layered waterproof product comprising a textile material covered with a film of a copolyetherester having an MVTR of at least 1000 g/m$^2$/24 hrs. (ASTM E96-66) having a thickness of 5 to 35 micrometers.

GB 2 024 100 discloses a flexible layered water resistant article comprising a microporous hydrophobic outer layer which is moisture vapour permeable but resist liquids and a hydrophilic inner layer of polyetherpolyurethane having a MVRR of above 1000/m$^2$/24 hrs.

However a problem with the films disclosed in the prior art is that the thickness at which the films can be readily extruded onto a support substrate is severely limited using standard extrusion techniques. Furthermore such films often require the addition of an adhesive in order to ensure permanent fixation of the coating to the substrate. However, this in turn detrimentally affects the overall moisture vapour permeability of the resulting composite.

Hence, there is a need to provide a composite structure which is liquid impermeable and moisture vapour permeable and which is readily processable so as to provide a thin film coating.

SUMMARY OF THE INVENTION

The present invention relates to a moisture vapour permeable liquid impervious composite substrate.

Said substrate comprises:
(a) a thermoplastic film made form a moisture vapour permeable thermoplastic composition having a complex viscosity of from 50 poise to 4000 poise at a frequency of 1 rad/s, at a temperature of 210° C. or less, and a complex viscosity of less than 2000 poise at a frequency of 1000 rad/s and at a temperature of 210° C. or less, said film having a thickness of less than 10 micrometers to 0.5 micrometers and
(b) a support layer, said support layer being moisture vapour permeable.

DETAILED DESCRIPTION OF THE INVENTION

Thus according to the present invention the composite structures comprise a thermoplastic film made form a moisture vapour permeable thermoplastic composition having a complex viscosity of from 50 poise to 4000 poise at a frequency of 1 rad/s, preferably from 100 poise to 2000 poise, more preferably from 100 poise to 1000 poise, at a temperature of 210° C. or less and a complex viscosity of less than 2000 poise, preferably less than 1000 poise, more preferably less than 500 poise, at a frequency of 1000 rad/s, at a temperature of 210° C. or less. In addition, said film has a thickness of from less than 10 micrometers to 0.5 micrometers, preferably from 9 micrometers to 0.5 micrometers, more preferably from 8 micrometers to 2 micrometers and most preferably from 7 micrometers to 2 micrometers. It has been surprisingly found that thermoplastic films made of thermoplastic compositions having the complex viscosity described allow for the films to be produced using typical techniques at the desired thinness. In particular the films of the present invention allow for films to be produced at greatly reduced thickness, whilst maintaining the mechanical properties of the film such that no failures concerning the uniformity of the film such as breakages or the presence of apertures arise.

Preferably, the present invention provides a composite material wherein the contribution of the polymeric film to the performance of the composite substrate resides only in the provision of a liquid barrier and hence should be provided as thinly as possible. The remaining performance physical criterion being provided by the provided support layer.

COMPOSITION OF THERMOPLASTIC FILM

According to the present invention the thermoplastic polymeric film is made form a moisture vapour permeable thermoplastic composition which comprises as an essential component from 5% to 100% by weight of said film of a polymer or mixture of polymers. Preferably the thermoplastic composition comprises from 10% to 80%, most preferably from 25% to 75% by weight of said polymer.

The suitable thermoplastic composition for the film of the present invention is selected such that the composition has the following complex viscosities ($\eta^*$):

50 poise<$\eta^*$<4000 poise, preferably 100 poise<$\eta^*$<2000 poise, more preferably 100 poise<$\eta^*$<1000 poise, at a frequency of 1 rad/s at a temperature of 210° C. or less and $\eta^*$<2000 poise, preferably $\eta^*$<1000 poise, more preferably $\eta^*$<500 poise, at a frequency of 1000 rad/s at a process temperature (T) of 210° C. or less, wherein $\eta^*$ represents the complex viscosity of the thermoplastic composition. Preferably the temperature T is 200° C. or less and more preferably 180° C. or less and most preferably from 200° C. to 50° C. It has been surprisingly found that polymeric films made form thermoplastic compositions having such viscosities are particularly suitable for coating processes and can provide very thin films.

Suitable polymers for use in the films according to the present invention include polyurethanes, poly-ether-amides block copolymers, polyethylene-acrylic acid copolymers, polyethylene oxide and its copolymers, poly actide and copolymers, polyamides, polyester block copolymers, sulfonated polyesters, poly-ether-ester block copolymers, poly-ether-ester-amide block copolymers, polyacrylates, poly-acrylic acids and derivatives, ionomers, polyethylene-vinyl acetate with a vinyl acetate content of more than 28% by weight, polyvinyl alcohol and its copolymers, polyvinyl ethers and their copolymers, poly-2-ethyl-oxazoline and derivatives, polyvinyl pyrrolidone and its copolymers, thermoplastic cellulose derivatives, and mixtures thereof. Particularly, preferred are polyurethanes, poly-ether-amides block copolymers, polyester block copolymers, and poly-ether-ester-amide block copolymers.

In addition to the thermoplastic polymeric component, the thermoplastic compositions also preferably further comprise a plasticiser or blend of plasticisers, preferably from 0% to 95%, more preferably from 20% to 90%, most preferably from 25% to 75% by weight of said thermoplastic composition. Suitable plasticisers include citric acid esters, tartaric acid esters, glycerol and its esters, adipates, sebacates, sorbitol, epoxidized vegetal oils, polymerised vegetal oils, polyols, phthalates, liquid polyesters, glycolates, p-toluene sulfonamide and derivatives, glycols and polyglycols, sorbitan esters, phosphates, monocarboxylic fatty acids ($C_8$–$C_{22}$) and their derivatives, and mixtures thereof. Particularly preferred plasticisers are citric and tartaric acid esters.

The thermoplastic compositions from which the polymeric films of the present invention are made may in addition comprise additional optional components to further improve the processibility of the film and mechanical characteristics as well as other characteristics as its tackiness, its resistance to ageing by light and oxygen, its visual appearance etc.

Such optional components include tackifying resins or blends of tackifying resins having a softening point of 125° C. or less. Preferred resins, which may be present by up to 50% by weight, may be selected from rosins and rosin esters, hydrocarbon resins, aliphatic resins, terpene and terpene-phenolic resins, aromatic resins, synthetic $C_5$ resins, mixtures of synthetic $C_5$–$C_9$ resins, and mixtures thereof. Other optional components of said thermoplastic composition include anti-oxidants, anti-ultraviolets, pigments and mixtures thereof, which may be present within the film at a level of up to 10% by weight of the thermoplastic composition.

The films of the present invention also preferably have a moisture vapour transport rate of at least 100 g/(m².24 hours), preferably at least 300 g/(m².24 hours), most preferably at least 500 g/(m².24 hours).

According to the present invention the composite structure further comprises as an essential element a support layer upon which the thermoplastic layer is typically directly coated. The support layer may be any useful layer provided that it is moisture vapour permeable, preferably having a moisture vapour permeability of at least 100 g/(m².24 hours), more preferably at least 300 g/(m².24 hours), and most preferably at least 500 g/(m².24 hours).

Suitable support layers for use herein include 2 dimensional, planar micro and macro-porous films; macroscopically expanded films; formed apertured films; nonwoven and woven layers. According to the present invention the apertures in said layer may be of any configuration, but are preferably spherical or oblong and may also be of varying dimensions. The apertures preferably are evenly distributed across the entire surface of the layer, however layers having only certain regions of the surface having apertures are also envisioned.

Suitable 2 dimensional porous planar layers of the backsheet may be made of any material known in the art, but are preferably manufactured from commonly available polymeric materials. Suitable materials are for example Goretex (TM) or Sympatex (TM) type materials well known in the art for their application in so-called breathable clothing. Other suitable materials include XMP-1001 of Minnesota Mining and Manufacturing Company, St. Paul, Minn., USA and Exxaire XBF-101W, supplied by the Exxon Chemical Company. As used herein the term 2 dimensional planar layer refers to layers having a depth of less than 1 mm, preferably less than 0.5 mm, wherein the apertures have an average uniform diameter along their length and which do not protrude out of the plane of the layer. The apertured materials for use as a backsheet in the present invention may be produced using any of the methods known in the art such as described in EPO 293 482 and the references therein. In addition the dimensions of the apertures produced by this method may be increased by applying a force across the plane of the backsheet layer (i.e. stretching the layer).

Suitable apertured formed films include films which have discrete apertures which extend beyond the horizontal plane of the garment facing surface of the layer towards the core thereby forming protuberances. The protuberances have an orifice located at its terminating end. Preferably said protuberances are of a funnel shape, similar to those described in U.S. Pat. No. 3,929,135. The apertures located within the plane and the orifices located at the terminating end of protuberance themselves maybe circular or non circular provided the cross sectional dimension or area of the orifice at the termination of the protuberance is smaller than the cross sectional dimension or area of the aperture located within the garment facing surface of the layer. Preferably said apertured performed films are uni directional such that they have at least substantially, if not complete one directional fluid transport towards the core.

Suitable macroscopically expanded films for use herein include films as described in for example in U.S. Pat. No. 4,637,819 and U.S. Pat. No. 4,591,523.

Preferred support layers for use herein include woven and nonwoven layers, most preferably hydrophobic fibrous layers such as hydrophobic non woven.

The composites of the present invention are particularly advantageous as they allow the possibility of providing a composite wherein the thermoplastic composition may be coated onto the support substrate as a film with the desired thickness. This is in contrast to current films which can only be extruded or coated onto the substrate relatively thickly. Typical coating conditions and apparatuses known in the art for the direct coating of low viscosities hot melts can be readily utilised in order to provide the thermoplastic composition at the required thickness.

A possible method for forming a composite laminate by coating the thermoplastic composition onto a substrate acting as a support layer is described in PCT application WO 96/25902.

At least at the coating temperature, the thermoplastic composition of the film preferably exhibits adhesive properties on the supportive layer such that no additional adhesive is required to achieve a permanent attachment between the film and the layer. In some applications it may be also desirable that the polymeric film remains tacky at any temperature i.e. it is formulated so to have the typical characteristics of a pressure sensitive adhesive.

The composite structures of the present invention find utility in a number of applications wherein liquid imperviousness and moisture vapour permeability are desirable. In particular the present invention can be effectively utilised within absorbent articles such as diapers, sanitary napkins, panty liners and incontinence products; perspiration pads such as underarm-, wrist- and head perspiration pads, collar inserts, shoe inserts, hat bands and breast pads; protective bedding covers, protective clothing and the like. Preferably the composite structures of the present invention have a moisture vapour transfer rate of at least 100 g/(m².24 hours), more preferably at least 300 g/(m².24 hours), and most preferably at least 500 g/(m².24 hours).

The composite structure of the present invention find particular utility as the backsheet for absorbent articles especially sanitary napkins and panty liners. Such articles will typically comprise components known to the skilled person such as a liquid previous topsheet, an absorbent core and backsheet and may optionally comprise fastening means, wings, and the like.

EXAMPLE

A polyether based thermoplastic polyurethane available from BF Goodrich Co.-USA commercialised under the trade name Estane 58245 was compounded with triethyl citrate available from Aldrich Co. and Irganox 1010 (anti oxidant agent) available from Ciba-Geigy.

| | |
|---|---|
| 30% | Estane 58245 |
| 69% | Triethyl Citrate |
| 1% | Irganox 1010 |

The blend was melt coated at 175° C. to obtain a film having a thickness equal to 5 $\mu$m. At the coating temperature it was found to have complex viscosities of 370 poise and 27 poise respectively at 1 and 1000 rad/s shear rate. The film was then laminated directly onto a 100% polyester spun-laced nonwoven 40 g/m² (support layer) commercialised under the trade name Fibrella 4100, available from Suominen (Finland). The composite substrate had a moisture vapour transfer rate of 1140 g/m².24 hrs.

According to the present invention the complex viscosity is measured using a Rheometer RDA-II available from Rheometrics Co. Water vapour permeability is measured at 23° C. according to the ASTM E-96 "Upright Cup" method.

What is claimed is:

1. A moisture vapour permeable liquid impervious composite substrate comprising:

(a) a thermoplastic film made from a moisture vapour permeable, liquid impervious, non water degradable thermoplastic composition, said composition comprising a blend of from 10% to 80% by weight of a polymer, and from 20% to 90% by weight of a plasticizer, wherein said polymer is selected from the group consisting of polyurethanes, poly-ether-amides block copolymers, polyester block copolymers, and poly-ether-ester-amide block copolymers and mixtures thereof; said composition having a viscosity of from 50 poise to 400 poise at any of 1 rad/s at a temperature of 210° C. or less and a viscosity of less than 2000 poise at a frequency of 1000 rad/s at a temperature of 210° C. or less; said film having a thickness of from 0.5 micrometers to 10 micrometers; and (b) a support layer, said layer being moisture vapour permeable;

wherein said composite substrate has a water vapour transfer rate of at least 300 g/m²/24 hrs at 23° C.

2. A moisture vapour permeable liquid impervious composite substrate according to claim 1, wherein said plasticisers are selected from citric acid esters and tartaric acid esters and mixtures thereof.

3. A moisture vapour permeable liquid impervious composite substrate according to claim 1, wherein said temperature from 50° C. to 200° C.

4. A moisture vapour permeable liquid impervious composite substrate according to claim 1, wherein said film has a thickness of from 0.5 micrometers to 9 micrometers.

5. A moisture vapour permeable liquid impervious composite substrate according to claim 1, wherein said temperature from 50° C. to 200° C.

6. An absorbent article comprising said composite substrate said film has a thickness of from 0.5 micrometers to 9 micrometers.

7. A moisture vapour permeable liquid impetuous composite substrate according to claim 1, wherein said film has a thickness of from 2 micrometers to 8 micrometers.

* * * * *

UNITED STATES PATENT AND TRADEMARK OFFICE
CERTIFICATE OF CORRECTION

PATENT NO. : 6,749,923 B1
DATED : June 15, 2004
INVENTOR(S) : Gianfranco Palumbo et al.

It is certified that error appears in the above-identified patent and that said Letters Patent is hereby corrected as shown below:

Column 2,
Line 23, delete "MVRR" and insert -- MVTR -- and delete "$1000/m^2/24hrs.$" and insert -- $1000\ g/m^2/24$ hrs. --.

Column 3,
Line 47, delete "actide" and insert -- lactide --.

Column 5,
Line 62, delete "previous" and insert -- pervious --.

Column 6,
Line 5, insert -- The final formulation in percent by weight had the following compositon: -- above the table.
Line 61, insert -- according to claim 1 wherein -- between "substrate" and "said".
Line 63, delete "impetuous" and insert -- impervious --.

Signed and Sealed this

Seventeenth Day of May, 2005

JON W. DUDAS
*Director of the United States Patent and Trademark Office*